United States Patent
Pichette

(10) Patent No.: US 12,201,783 B1
(45) Date of Patent: Jan. 21, 2025

(54) USE OF BLUE-LIGHT FILTERING EYEGLASSES FOR TREATMENT OF RESTLESS LEGS SYNDROME

(71) Applicant: Steven F Pichette, Warwick, RI (US)

(72) Inventor: Steven F Pichette, Warwick, RI (US)

( * ) Notice: Subject to any disclaimer, the term of this patent is extended or adjusted under 35 U.S.C. 154(b) by 0 days.

(21) Appl. No.: 18/584,386

(22) Filed: Feb. 22, 2024

Related U.S. Application Data

(60) Provisional application No. 63/536,640, filed on Sep. 5, 2023.

(51) Int. Cl.
*G02C 7/10* (2006.01)
*A61M 21/02* (2006.01)
*A61M 21/00* (2006.01)

(52) U.S. Cl.
CPC ............... *A61M 21/02* (2013.01); *G02C 7/10* (2013.01); *A61M 2021/0044* (2013.01)

(58) Field of Classification Search
CPC .. A61M 21/02; A61M 2021/0044; G02C 7/10
USPC ...................................... 600/26, 27
See application file for complete search history.

(56) References Cited

U.S. PATENT DOCUMENTS

| | | | | |
|---|---|---|---|---|
| 6,602,868 B2 * | 8/2003 | McBrinn | ............. | A61K 31/519 514/230.2 |
| 7,644,715 B2 * | 1/2010 | Hayes | ................... | A61B 18/24 607/101 |
| 8,623,913 B2 * | 1/2014 | Melnick | .................. | A61P 21/00 560/163 |
| 9,017,273 B2 * | 4/2015 | Burbank | ............ | A61H 23/0218 601/46 |
| 9,808,620 B2 * | 11/2017 | Kent | .................. | A61N 1/36003 |
| 2021/0169417 A1 * | 6/2021 | Burton | ................ | A61B 5/4857 |
| 2023/0321429 A1 * | 10/2023 | Oxenrider | ............ | A61N 1/0452 |

OTHER PUBLICATIONS

Dr. Banu Tasci Fresko "Restless Legs Syndrome", 2019, (https://www.banutascifresko.com/health-101/restless-legs-syndrome/?lang=en) (Year: 2019).*

* cited by examiner

*Primary Examiner* — Tuyen Tra
(74) *Attorney, Agent, or Firm* — Feeney IP Law; Daniel W. Sullivan; Alan F. Feeney

(57) ABSTRACT

A method of using blue-light filtering eyeglasses for the treatment of symptoms associated with restless legs syndrome is provided. The method involves providing eyeglasses that can block or filter-out blue-light, wearing the eyeglasses beginning at dusk for a time period of at least two hours while being exposed to blue-light; and removing the eyeglasses, whereby the symptoms associated with restless legs syndrome are reduced. Preferably, the user wears the blue-light filtering eyeglasses for a period of about two to about six hours between the time of dusk and sunrise while being exposed to blue-light.

7 Claims, No Drawings

USE OF BLUE-LIGHT FILTERING EYEGLASSES FOR TREATMENT OF RESTLESS LEGS SYNDROME

CROSS-REFERENCE TO RELATED APPLICATIONS

The application claims the benefit of U.S. Provisional Patent Application No. 63/536,640 filed Sep. 5, 2023, the entire disclosure of which is hereby incorporated by reference.

BACKGROUND OF THE INVENTION

Field of the Invention

The present invention relates generally to a method of using blue-light filtering eyeglasses for the treatment of symptoms associated with restless leg syndrome. The method of the invention has a calming effect on restless leg syndrome symptoms.

Brief Review of the Related Art

In general, restless leg syndrome is a medical condition that causes a person to have discomfort and unpleasant sensations in the legs. When a person is resting, the onset of restless legs syndrome can force the person to stand-up and walk/run to relieve the discomfort and sensations. The symptoms are especially uncomfortable when a person is trying to sleep. The symptoms also can occur when a person is sitting for long periods of time such as in a car trip.

The painful symptoms of restless legs syndrome include tingling, burning, aching, and jumpiness of the leg, and the like. A person has compulsion to move their legs, and he/she will try different techniques to relieve these sensations. For example, a person may try walking and other deliberate movements to quiet the legs down. However, these actions often do not alleviate the bothersome symptoms of restless legs syndrome. On the other hand, if the person decides to stay still and relax, this may cause further discomfort. Sometimes, the person will show an involuntary jerking of the legs.

There are many proposed treatments for restless legs syndrome. These include minimizing the intake of caffeine, alcohol, and nicotine before sleeping. There are also pharmaceutical treatments, such as with benzodiazepines, dopamine, anti-convulsion medication, opioids, and the like. However, there can be side effects of such medications including drowsiness during the time when a person is awake and there may be some cognitive issues over a long period of time.

In recent years, new methods have been developed for treating restless legs syndrome using some form of electro-stimulation or compression. For example, Lozano, U.S. Pat. No. 7,774,068 relates generally to systems and methods for treating movement disorders (for example, restless leg syndrome) using cortical stimulation. In one embodiment, a method for treating the movement disorder comprises determining a site at the cortex of the brain of a patient related to the afflicted body part. The cortical stimulation increases dopamine release.

Matsen, U.S. Pat. No. 8,939,303 is directed to a therapeutic device for treating symptoms related to restless leg syndrome. The device uses electrical stimulation and comprises a remote, a pair of pads, a plurality of electrodes, and a fastener assembly. The range of the electricity generator has a voltage range of approximately twenty-five volts, which is a safe current output according to the '303 Patent. The electrical current causes constant muscle contractions at a desired strength.

Burbank et al., U.S. Pat. No. 9,017,273 is also directed to devices and methods for treating restless leg syndrome. The device is configured to generate counter-stimulation in a patient suffering from the syndrome. The counter-stimulation of amplitude, intensity, and time duration is lower than that which would wake the patient and higher than that sufficient to relieve the symptoms and allow the patient to return to sleep.

Morgenlander, U.S. Patent Application Publication 2003/0176822 relates to a method of treating restless leg syndrome in a patient in need of such treatment includes applying positive pressure to an extremity of the patient at a magnitude and for a duration sufficient to combat the symptoms. The device includes a pressure sleeve and source. In certain embodiments, the method comprises applying a pressure at a magnitude of between about 5- and 80-mm Hg to the extremity of the patient. In other embodiments, the method comprises applying the pressure intermittently for intervals of between about 5 seconds and 30 minutes.

However, the foregoing patent references do not disclose using blue-light filtering eyeglasses for the treatment of restless leg syndrome symptoms. The present invention provides such methods. Other advantages and benefits of the present invention are described further below.

SUMMARY OF THE INVENTION

The present invention provides methods for treating one or more symptoms associated with restless legs syndrome. The methods involve providing eyeglasses that can block or filter-out blue-light, wearing the eyeglasses between dusk and sunrise for a period of at least two hours while being exposed to blue-light; and then removing the eyeglasses, whereby the symptoms associated with restless legs syndrome are reduced. Preferably, the eyeglasses are worn for a period of about two to about six hours. In one preferred embodiment, the eyeglasses have blue-light filtering yellow-colored lenses. In another preferred embodiment, the eyeglasses have amber-colored blue-light filtering lenses. In one preferred embodiment, the blue-light filtering lenses block blue light having a wavelength in the range of about 400 nm to about 550 nm.

DETAILED DESCRIPTION OF THE INVENTION

The present invention relates generally to methods for treating one or more symptoms associated with restless legs syndrome. The methods involve a first step of providing eyeglasses that can block or filter-out blue-light, a second step of wearing the eyeglasses, preferably at dusk for a period of at least two hours, while being exposed to blue-light. More preferably, the eyeglasses are worn between the times of sunset and sunrise for a period of at least two hours. By the term, "sunrise" or "sunset", it is meant the time when an observer at sea level, with an unimpeded view of the horizon, sees the upper disc of the sun to be tangent to (touching) the horizon. By the term, "dusk", it is meant the point when the sun is at 18 degrees below the horizon and there is no longer any sunlight in the sky. It is the darker stage of twilight. That is, dusk is the time just before night when the daylight has gone but when it is not completely dark. The third step involves removing the eyeglasses. By following these steps, the symptoms associated with restless legs syndrome are reduced. In one preferred embodiment, a user can wear the blue-light filtering eyeglasses for at least two hours from the times of sunset to sunrise. The period of time that it takes to get dark after the exact time of sunset can vary depending upon several factors. These factors include, for example, geographical location, time of year, and atmospheric conditions. The exact times of sunset and sunrise can be established by weather, calendar, and other computer programs and applications. Preferably, in accordance with the present invention, the blue-light filtering eyeglasses are worn for a period of about two to about six hours after the user places them on. In one preferred embodiment, the eyeglasses have yellow-colored lenses. In another preferred embodiment, the eyeglasses have amber-colored lenses. In one preferred embodiment, the blue-light filtering lenses of the eyeglasses block blue light having a wavelength of 400 nm to about 550 nm.

In general, many light sources transmit some blue-light. The visible light spectrum generally ranges from long wave red light (about 700 nm) to short wavelength violet light (about 380 nm). Human beings have a natural optical network that blocks some natural blue-light in the visible light spectrum. However, natural blue-light, which is emitted from the sun, is not completely blocked, because it has some health benefits. For example, natural blue-light helps to regulate a person's internal biological clock and helps with generating natural sleep patterns.

In recent years, more people have developed eye and vision problems from Light-Emitting Diodes (LEDs) and Liquid Crystal Displays (LCDs), computer monitors, laptops, tablets, televisions, cellular phones, and the like. These devices emit an artificial type of blue-violet light which can have harmful eye and vision effects. In general, the blue-light spectrum is about 400 nm to about 550 nm. At nighttime, the transmission of artificial blue light to a person can be particularly troublesome. It is believed that blue-light emitted from LEDs, LCDs, personal computers, laptops, tablets, televisions, cellular phones, and the like can stimulate the brain and nervous system making it difficult for many people to fall asleep at nighttime. More particularly, many people who suffer from Restless Legs Syndrome (RLM) appear to have heightened sensitivity to blue-light that is transmitted by such devices. The emitted blue-light can cause many people to have a greater amount of restless legs syndrome such as Periodic Leg Movements (PLMs) which are discussed further below. In accordance with the methods of the present invention, it has now been found that using blue-light filtering glass can reduce the amount of such restless leg syndrome symptoms.

Blue-light filtering eyeglasses having filters that block or absorb blue-light have been developed and are generally known in the eyeglasses industry. A wide variety of blue-light filtering eyeglasses (sometimes referred to as computer eyeglasses) are commercially-available and can be used in the methods of the present invention. In general, blue-light filtering eyeglasses having clear lenses block about 20% to about 50% of the transmitted blue-light. Meanwhile, blue-light filtering eyeglasses having yellow-colored lenses can block about 50% to about 70% of the transmitted blue-light. On the other hand, blue-light filtering eyeglasses having amber-colored lenses can block greater than about 70% of the transmitted blue-light. Finally, red-colored lenses can block up to 100% of the transmitted blue-light.

The advantages of using blue-light filtering eyeglasses over all other conventional treatment methods for restless legs syndrome in accordance with the present invention include, but are not limited to, 1) the blue-light filtering eyeglasses are completely non-invasive to the user; 2) the blue-light filtering eyeglasses are easily adapted to each person, wherein the exact time that a person needs to wear the eyeglasses and strength of the glasses needed may vary from person-to-person; 3) there are no known side effects to a person wearing the blue-light filtering eyeglasses; 4) the blue-light filtering eyeglasses are relatively low cost; 5) the blue-light filtering eyeglasses work for both men and women.

The present invention is further illustrated by the following Examples, but these Examples should not be construed as limiting the scope of the invention.

EXAMPLES

In Example 1, Patient A had symptoms of tingling and aching in their legs, and other symptoms of restless legs syndrome. Patient A did a self-evaluation, and he reported a Rating of 5 on the Symptoms Scale as described further below. Patient A then wore a pair of blue-light filtering glasses (yellow-colored lenses) for a period of about 3 hours while being exposed to blue-light. Patient A wore the blue-light filtering eyeglasses at nighttime. After this time period, Patient A removed the glasses and did a self-evaluation of his symptoms. Patient A reported a Rating of 2 on the Symptoms Scale.

Patient B had symptoms of involuntary jerking of their legs, and other symptoms of restless legs syndrome. Patient B did a self-evaluation, and he reported a Rating of 4 on the Symptoms Scale as described further below. Patient B then wore a pair of blue-light filtering glasses (yellow-colored lenses) for a period of about 4 hours while being exposed to blue-light. Patient B wore the blue-light filtering eyeglasses at nighttime. Patient B then removed the glasses and did a self-evaluation of his symptoms. Patient B reported a Rating of 3 on the Symptoms Scale.

Patient C had symptoms of involuntary jerking of their legs, jumpiness, and other symptoms of restless legs syndrome. Patient C did a self-evaluation, and he reported a Rating of 5 on the Symptoms Scale as described further below. Patient C then wore a pair of blue-light filtering glasses (amber-colored lenses) for a period of about 6 hours while being exposed to blue-light. Patient C wore the blue-light filtering eyeglasses at nighttime. Patient C then removed the glasses and did a self-evaluation of his symptoms. Patient C reported a Rating of 1 on the Symptoms Scale. These results are reported in Table 1 below.

TABLE 1

| Symptoms of Restless Legs Syndrome | Scale |
| --- | --- |
| Severe Symptoms | 5 |
| Moderate Symptoms | 4 |
| Some Symptoms | 3 |
| Mild Symptoms | 2 |
| No Symptoms | 1 |

Example 2

In Example 2, Patient D wore a pair of blue-light filtering glasses (amber-colored lenses) for a period of about 2 hours per 24 hour-day over a period of 30 days while being exposed to blue-light. Patient D wore the blue-light filtering eyeglasses during the time period from sunset to sunrise. Later, Patient D was examined at a Sleep Center according to the following conditions.

Sleep Architecture—The sleep exam for Patient D started at 09:38 PM and ended at 06:10 AM with a sleep latency of 11.5 minutes and a REM latency of 309.0 minutes. Total sleep time was 283.0 minutes with a sleep efficiency of 55.33%. The sleep stage percentages were 2.1% for N1 stage; 54.8% for N2 stage; 25.1% for N3 stage; and 18.0% REM. The total time of Patient D being awake was 216.0 minutes and there were 168 spontaneous arousals.

Periodic Limb Movements (PLM)—The total PLM Index was 19.5 per hour of sleep. The total number of leg movements that caused arousal was 15 for a leg movement arousal index of 3.2.

Control Example 2A

In a control sleep study (Control Example 2A), Patient D did not wear blue-light filtering glasses, and he was examined at a Sleep Center according to the following conditions.

Sleep Architecture—The sleep exam for Patient D started at 11:11 PM and ended at 05:32 AM with a sleep time of 342.5 minutes and total REM sleep of 45 minutes with a sleep efficiency of 89.84%. The sleep stage percentages were 2.2% for N1 stage; 53.7% for N2 stage; 2.9% for N3 stage; 28.0% for N4 stage; and 13.1% REM. Patient D had Periodic Leg Movements (PLM) as reported in Table 2A below.

TABLE 2A

| Type | Movements | Number Index*(Number per hour of sleep) |
| --- | --- | --- |
| PLM Arousals | 66 | 11.6 |
| Isolated Limb Movements | 101 | 28.2 |
| Periodic Limb Movements | 195 | 34.2 |
| Total Movements | 355 | 62.2 |

Control Example 2B

In a control sleep study (Control Example 2B), Patient D did not wear blue-light filtering glasses, and he was examined at a Sleep Center according to the following conditions.

Sleep Architecture—The sleep exam for Patient D started at 09:05 PM and ended at 04:51 AM with a total sleep time of 415.5 minutes and total REM sleep of 58 minutes with a sleep efficiency of 89.2%. The sleep stage percentages were 5.8% for N1 stage; 76.2% for N2 stage; 4.1% for N3 stage; and 13.1% REM. Patient D had Periodic Leg Movements (PLM) as reported in Table 2B below.

TABLE 2B

| Type | Movements | Number Index*(Number per hour of sleep) |
| --- | --- | --- |
| PLM Arousals | 5 | 0.7 |
| Isolated Limb Movements | 0 | 0 |
| Periodic Limb Movements | 432 | 62.4 |
| Total Movements | 432 | 62.4 |

As demonstrated in the above Control Examples 2A and 2B, Patient D did not wear blue-light filtering glasses before being examined at the Sleep Center; and the following Periodic Limb Movement indices were reported: 62.2 per hour and 62.4 per hour. In contrast, as demonstrated in Example 2, Patient D did wear blue-light filtering glasses before being examined at the Sleep Center; and the following Periodic Limb Movement index was reported: 19.5 per hour. These results are summarized below in Table 3 below.

TABLE 3

| Wearing of Blue-Light Filtering Glasses | Limb Movement Index |
| --- | --- |
| None - Patient D did not wear blue-light filtering glasses before being subjected to the Sleep Study. (Example 2A) | 62.2 per hour |
| None - Patient D did not wear blue-light filtering glasses before being subjected to the Sleep Study. (Example 2B) | 62.4 per hour |
| Yes - Patient D wore blue-light filtering glasses for about 2 hours per a 24 hour day over a period of 30 days before being subjected to the Sleep Study (Example 2) | 19.5 per hour |

As demonstrated in the above Example, the method of the present invention for treating one or more symptoms associated with restless legs syndrome is effective. Patient D wore the blue-light filtering glasses while being exposed to blue-light and then removed the glasses as described in Example 2. For Patient D, upon following the method of using and removing the blue-light filtering glasses in accordance with the present invention, their symptoms associated with restless legs syndrome were significantly reduced as particularly evidenced by a decrease in their Limb Movement Index of 68% (Example 2 Index versus Example 2A Index) and 68% (Example 2 Index versus Example 2B index). Preferably, the symptoms associated with restless legs syndrome are reduced by at least 50% and more preferably by at least 60% in accordance with the present invention. In one embodiment, the symptoms associated with restless legs syndrome are reduced in the amount of 60% to 80%.

It should be understood the systems, methods, processes, and the like described and illustrated herein represent only some embodiments of the invention. It is appreciated by those skilled in the art that various changes and additions can be made to the systems, methods, processes, and the like without departing from the spirit and scope of this invention. It is intended that all such embodiments be covered by the appended claims.

I claim:

1. A method of treating one or more symptoms associated with restless legs syndrome, comprising the steps of:
   providing eyeglasses having blue-light filtering lenses to a user; wherein the user wears the eyeglasses between the time of dusk and sunrise for a time period of at least two hours while being exposed to blue-light; and then removing the eyeglasses from the user so that the symptoms associated with restless legs syndrome are reduced.

2. The method of claim 1, wherein the user wears the eyeglasses between the time period of dusk and sunrise for a period of about two hours to about six hours.

3. The method of claim 1, wherein the blue-light filtering lenses are yellow-colored.

4. The method of claim 1, wherein the blue-light filtering lenses are amber-colored.

5. The method of claim 1, wherein the blue-light filtering lenses block blue-light having a wavelength of 400 nm to about 550 nm.

6. The method of claim 5, wherein the blue-light is emitted from a device containing Light-Emitting Diodes or Liquid Crystal Displays.

7. The method of claim 6, wherein the device is selected from the group consisting of personal computers, laptops, tablets, televisions, cellular phones, and combinations thereof.

\* \* \* \* \*